United States Patent [19]

Michalski et al.

[11] Patent Number: 4,470,933
[45] Date of Patent: Sep. 11, 1984

[54] PREPARATION OF S-BROM-DITHIOPHOSPHORIC, DITHIOPHOSPHONIC AND DITHIOPHOSPHINIC ACID DERIVATIVES

[75] Inventors: Jan Michalski; Marek Potrzebowski, both of Lód ; Andrzej Lopusinski, Pabianice, all of Poland

[73] Assignee: Bayer Aktiengesellschaft, Leverkusen, Fed. Rep. of Germany

[21] Appl. No.: 433,338

[22] Filed: Oct. 8, 1982

Related U.S. Application Data

[62] Division of Ser. No. 324,492, Nov. 24, 1981, Pat. No. 4,369,147.

[30] Foreign Application Priority Data

Dec. 10, 1980 [PL] Poland ................................... 228376

[51] Int. Cl.³ .......................... C07F 9/165; C07F 9/28
[52] U.S. Cl. ..................................... 260/986; 564/12; 568/14
[58] Field of Search ......................... 260/986; 564/12; 568/14

[56] References Cited

FOREIGN PATENT DOCUMENTS 0053787 6/1982 European Pat. Off. ............ 260/986

OTHER PUBLICATIONS

Michalski et al., "Chem. & Ind.", No. 37, (1958), pp. 1199–1200.
Chemical Abstracts, vol. 52, p. 6156.

Primary Examiner—Anton H. Sutto
Attorney, Agent, or Firm—Sprung, Horn, Kramer & Woods

[57] ABSTRACT

A compound of the formula

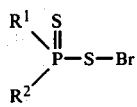

in which $R^1$ and $R^2$ each independently is an optionally substituted alkyl, aralkyl, aryl, alkoxy, aryloxy, aralkoxy, alkylthio, arylthio, aralkylthio, alkylamino, arylamino or aralkylamino radical, is produced by reacting a compound of the formula

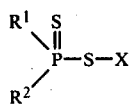

in which X is hydrogen, an alkali metal ion, an optionally alkyl- ,aralkyl- and/or aryl-substituted ammonium radical, a trialkylsilyl radical, or

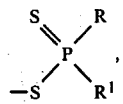

with bromine in the presence of an inert diluent at a temperature from about −50° to 20° C.

The product can be employed as a flame retardant, a vulcanizing accelerator and/or an intermediate for synthesizing pesticides.

2 Claims, No Drawings

PREPARATION OF S-BROM-DITHIOPHOSPHORIC, DITHIOPHOSPHONIC AND DITHIOPHOSPHINIC ACID DERIVATIVES

This is a division of application Ser. No. 324,492 filed Nov. 24, 1981, now U.S. Pat. No. 4,369,147.

This invention relates to certain new dithiophosphoric, dithiophosphonic and dithiophosphinic acid bromides, their preparation and their use as intermediates in making derivatives of phosphor-dithioic acids which have been found useful as insecticides, fungicides, herbicides, and the like.

Compounds of structure and reactivity characteristic of pseudohalogens are important commercially, e.g. chlorides, sulphenyl esters, sulphenamides and disulfides of the general formula

RR'P/S/SX wherein
R=R'=Alkyl;
R=R'=O-Alkyl;
R'=O-Alkyl and
R=Alkyl;
X=Cl or —O-Alkyl;
—N-Alkyl$_2$;
—S-Alkyl;
—S-Aryl;

—SP/CF$_3$/$_2$ and
—SP/S/RR'.

Many of these compounds are applicable directly or may be applied as substrates for the synthesis of dithiophosphoric acid derivatives. However, most of the above mentioned phosphordi-thioacid derivatives of biological activity, cannot be prepared in a one step synthesis. This results in a decrease in the overall yield as well as an increase in cost. For example, up to now such P-S-chlorides were obtained by splitting of the sulphur-nitrogen bond by hydrogen chloride in P-S-N amides. This method is inconvenient because on the one hand the sulfenamides used as substrates are not readily available and, on the other hand, the product obtained is impure and its purification is difficult.

It is accordingly an object of the invention to provide a one step synthesis for making novel bromides which are useful per se and as intermediates.

Specifically novel dithiophosphoric, dithiophosphonic and dithiophosphinic acid S-bromides are prepared by reaction of substantially equimolar quantities of bromine and a compound of the general formula

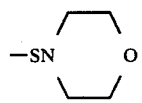

in which
R and R' each independently is an optionally substituted alkyl, aralkyl, aryl, alkoxy, aryloxy, aralkoxy, alkylthio, arylthio, aralkylthio, alkylamino, arylamino or aralkylamino radical, X is hydrogen, an alkali metal ion, an optionally alkyl-, aralkyl- and/or aryl-substituted ammonium radical, a trialkylsilyl radical, or

R'' is C$_{1-4}$ alkyl.

Advantageously, unless otherwise defined alkyl moieties have from about 1 to 5 carbon atoms, aryl is phenyl, aralkyl is benzyl or phenethyl.

Thus the reactants are dithioic acids of the formula

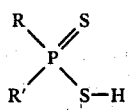

their salts of the formula

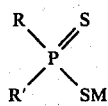

wherein M is sodium, potassium or an ammonium radical, trialkylsilyl dithioic acid esters of the formula

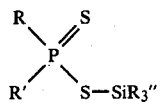

and disulfides of the formula

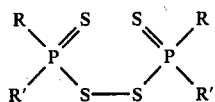

A solution or suspension of the starting material in an aprotic solvent is mixed with a solution of bromine in a similar solvent. The reaction is generally carried out with cooling, advantageously below about 15° C., and preferably from about 5° C. down to −25° C.

As aprotic solvents there can be employed carbon tetrachloride, chloroform, dichloromethane, benzene and petroleum ether of b.p. 20°–40° C. According to the invention the product is obtained in yields in the range of 80–90% as confirmed by $^{31}$P nuclear magnetic resonance analysis. The crude products may be directly applied as flame retardants, as vulcanizing accelerators due to their ready liberation of sulphur, as well as intermediates in pesticide systheses.

The following examples illustrate the novel process for preparing the sulphenyl bromides of the present invention, without being limiting:

EXAMPLE 1

Into a 250 ml three neck flask fitted with mechanical stirrer, thermometer and dropping funnel were placed 34.2 grams (0.1 mole) of O,O-bis-(2,2-dimethyl-propyl)-dithiophosphoric acid S-trimethylsilyl ester and 100 ml of carbon tetrachloride. To this solution, stirred continuously and maintained at −15° C., 16.0 grams (0.1 mole) of bromine in 10 milliliters of carbon tetrachloride were added dropwise. After the addition was completed the stirring was continued for an additional 30 minutes. The solvent and trimethylbromsilane were removed under a pressure of 10 mm Hg at 0°–5° C.

34.0 Grams of a yellow oily liquid were obtained. It was identified as S-brom-dithiophosphoric acid-O,O-di(2,2-dimethylpropyl)-ester by nuclear magnetic resonance analysis $\delta_{31p}$=74.4 ppm/neat relative to 85% $H_3PO_4$/.

Analysis: Calculated for $C_{10}H_{22}O_2PS_2Br$, %: C=34.38; H=6.34; P=8.86. Found, %: C=33.80; H=6.50; P=9.00.

EXAMPLE 2

To a stirred solution of 31.4 grams (0.1 mole) of bis-(dimethoxy-thio-phosphoryl)-disulphide in 80 ml of chloroform at −20° C. 16.07 grams (0.1 mole) of bromine dissolved in 10 ml of chloroform were added dropwise. Stirring was continued for 20 minutes. Then the solvent was evaporated, at −5°–0° C. under a pressure of 5 mm Hg/. In this manner 40.0 grams of S-brom-dithiophosphoric acid- O,O-dimethyl ester were obtained. The analysis of the resulting product with the aid of $^{31}$P NMR showed absorption at 79.9 ppm /CHCl$_3$/ relative to 85% $H_3PO_4$. To confirm the identity of the product it was allowed to react with cyclohexene, forming O,O-dimethyl-S-(2-bromocyclohexyl)-dithiophosphoric acid ester, b.p. 110° C. at 0.01 mm Hg/. Nuclear magnetic resonance analysis /85% $H_3PO_4$ as a standard/ indicated $\delta_{31p}$ equal +92.3 ppm.

Analysis: Calculated for $C_{16}H_{32}O_2PS_2Br$, %: C, 44.56H, 7.42; P, 7.18. Found: C, 44.91; H, 7.62; P, 7.26.

EXAMPLE 3

Into a vigorously stirred suspension of 10.3 grams (0.05 mole) of the sodium salt of O-methyl-t-butane-dithiophosphonic acid ester in 50 ml of petroleum ether, b.p. 20 to 40° C. at −25° C. 8 grams (0.05 mole) of bromine dissolved in 10 ml of petroleum ether were dropped. The sodium bromide was filtered off in the closed system. Then the solvent was driven off under a pressure of 3 mm Hg at −5 to 0° C. In this manner S-brom-O-methyl-t-butane dithio-phosphonic acid ester was obtained as a yellow oily liquid in a yield 93%, based on $^{31}$p NMR spectra/. The nuclear magnetic resonance analysis /85% $H_3PO_4$ as a standard/$\delta_{31p}$ equal +110.7 ppm.

EXAMPLE 4

Into a stirred solution of 11.3 grams (0.04 mole) of O,O-diphenyl-dithiophosphonic acid ester in 15 ml of benzene and 20 ml $CH_2Cl_2$ at −10° C. 6.4 grams (0.04 mole) of bromine was added dropwise. Stirring was continued for 20 minutes. Then the solvent was driven off under a pressure of 5 mm Hg at 0° C. 14.4 Grams of S-brom-O,O-diphenyl-dithiophosphoric acid ester was obtained as a yellow, oily liquid. It solidified at −20° C. Nuclear magnetic resonance analysis /85% $H_3PO_4$ as a standard/ indicated $\delta_{31p}$ equal +69.8 ppm/CCl$_4$/.

Analysis: Calculated for $C_{12}H_{10}O_2PS_2Br$, %: C=39.87; H=2.80; P=8.57. Found: C=40.01; H, 2.60, P, 8.95.

It will be understood that the specification and examples are illustrative but not limitative of the present invention and that other embodiments within the spirit and scope of the invention will suggest themselves to those skilled in the art.

What is claimed is:

1. A process for the preparation of a compound of the formula

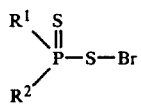

in which $R^1$ and $R^2$ each independently is an optionally substituted alkyl, aralkyl, aryl, alkoxy, aryloxy, aralkoxy, alkylthio, arylthio, aralkylthio, alkylamino, arylamino or aralkyamino radical, comprising reacting a compound of the formula

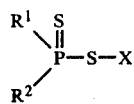

in which X is hydrogen, an alkali metal ion, an optionally alkyl-, aralkyl- and/or aryl-substituted ammonium radical, a trialkylsilyl radical, or

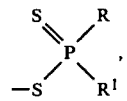

with an approximately equimolar amount of bromine in the presence of an inert diluent at a temperature from about −25 to 5° C.

2. A process according to claim 1, wherein the inert diluent is an aprotic solvent.

* * * * *